US00PP27249P3

(12) United States Plant Patent
Miller et al.

(10) Patent No.: US PP27,249 P3
(45) Date of Patent: Oct. 11, 2016

(54) SATSUMA HYBRID NAMED 'SONET'

(50) Latin Name: ***Citrus unshiu* X**
Varietal Denomination: Sonet

(71) Applicant: AGRICULTURAL RESEARCH COUNCIL, Hatfield, Pretoria (ZA)

(72) Inventors: James Edwin Miller, Addo (ZA); Nicola Kim Combrink, Addo (ZA); Johannes Gerhardus Jooste Maritz, Port Elizabeth (ZA)

(73) Assignee: AGRICULTURAL RESEARCH COUNCIL, Hatfield Pretoria (ZA)

( * ) Notice: Subject to any disclaimer, the term of this patent is extended or adjusted under 35 U.S.C. 154(b) by 392 days.

(21) Appl. No.: 13/573,528

(22) Filed: Sep. 21, 2012

(65) Prior Publication Data

US 2014/0090121 P1 Mar. 27, 2014

(51) Int. Cl.
*A01H 5/08* (2006.01)

(52) U.S. Cl.
USPC ..... Plt./202
CPC ..... *A01H 5/0806* (2013.01)

(58) Field of Classification Search
USPC ..... Plt./202
See application file for complete search history.

(56) References Cited

U.S. PATENT DOCUMENTS

| | | | | |
|---|---|---|---|---|
| PP13,617 | P2 * | 3/2003 | Vardi et al. | Plt./202 |
| PP22,062 | P3 * | 8/2011 | de Teresa Cortes | Plt./202 |
| PP23,496 | P2 * | 3/2013 | Moy et al. | Plt./201 |
| 2011/0055988 | P1 * | 3/2011 | Cortes | Plt./202 |

OTHER PUBLICATIONS

Citrogold (retrieved from internet search Feb. 26, 2015).*
UPOV Record Detail (retrieved from UPOV search on Feb. 26, 2015).*

* cited by examiner

*Primary Examiner* — Keith Robinson
(74) *Attorney, Agent, or Firm* — Birch, Stewart, Kolasch & Birch, LLP

(57) ABSTRACT

A new Satsuma hybrid (*Citrus unshiu* X) designated the variety name of 'Sonet' is described. The novel characteristics of the fruit include early maturity, tighter rind and firmer fruit does not puff easily and has an improved flavour compared to known varieties of Satsuma ripening at this time.

6 Drawing Sheets

Botanical/commercial classification: (*Citrus unshiu* X), new hybrid Satsuma variety.

Variety denomination: 'Sonet'.

BACKGROUND OF THE INVENTION

'Sonet' is an open pollinated hybrid of an unpatented *Citrus unshiu* variety 'Miho Wase' (unpatented) (the female seed parent). In 1996 open pollinated fruit was collected from 'Miho Wase' trees adjacent to *Citrus reticulata* varieties 'Nova tangelo' (unpatented), 'Ellendale' (unpatented) and 'Novelty' (unpatented) (possible male pollen parents). The seeds from each fruit were extracted and planted. Zygotic seedlings were selected in the nursery in 1997, by leaf morphology. The 14 selected seedlings were budded to 'Troyer citrange' (unpatented) rootstocks and planted on a trellising and arching system in a forcing house, in 1998, situated in Addo, in the Eastern Cape province of the Republic of South Africa (global positioning satellite coordinates 25° 42'E.; 33° 34'S.). Due to the early maturing and fruiting of *citrus* trees grown on the trellising and arching system, the first fruit was set in 2000. These trees were then evaluated for fruit quality traits. Based on the results of this evaluation, one of the aforementioned trees was selected for further evaluation, resulting in the present 'Sonet' variety. 'Sonet' was made subject of a South African Plant Breeders' Rights application on 5 Dec. 2006. This application was subsequently granted in 2009 under number ZA 20094289.

The time of fruit maturity (early to mid April), makes this selection an early maturing variety. Good flavour (mandarin-like) and firm fruit with a good shelf life of at least four weeks from maturity make 'Sonet' superior to the 'Satsuma' (unpatented) and early 'Clementine' (unpatented) in the market at this time.

Trees bear a good to excellent crop from the fourth year after planting. Alternate-bearing has not been noted. There is a small percentage of splitting in February and as with all early maturing mandarin cultivars, some fruit are lost to sunburn.

'Sonet' was first asexually propagated in Addo, South Africa in 2000 when buds were collected from a hybrid seedling designated WH/B/02/36 (1740). Three trees were topworked onto 'Carrizo citrange' (unpatented) rootstocks and one tree onto a 'Rosehaugh' (unpatented) mandarin rootstock. These four trees of 'Sonet' were initially used for evaluation and description purposes. Two more trees were top worked onto 'F80/9 citrumelo' (unpatented) rootstocks in 2001 for evaluation purposes. In 2005 three budded nursery trees were planted out on 'Troyer citrange' rootstocks for evaluation. The first trialorchard of 'Sonet' was planted at Addo in February 2006. This consisted of budded nursery trees, 125 trees on 'Carrizo citrange' rootstock and 19 trees on 'Troyer citrange' rootstock. In 2009 a further 24 budded nursery trees on C35 rootstock and four trees on 'Carrizo citrange' rootstock were planted for evaluation. All characteristics of the original tree and its fruit as determined and described appear to be transmitted through succeeding asexual propagations. No incompatibility or other rootstock related problems have yet been observed. The mother tree is still growing in the forcing house on the trellising and arching system in a 20 liter pot, as of 2012, 14 years old. The tree is in a fair condition and is still bearing good quality fruit.

Further, 'Sonet' has been cleansed of all graft transmissible viruses and viroids by shoot-tip grafting (STG), followed by pre-immunization with a light strain of the *Citrus tristeza* virus (LMS6). This was done through a regulated process, which involves taking vegetative buds from the mother tree and introducing the same into the South African *Citrus* Improvement Scheme. In this process, plant material is shoot-tip grafted to provide a virus-free source of bud wood material. Material so obtained is then pre-immunized with a mild strain of the aforementioned *Citrus tristeza* virus, followed by a certification by the relevant South African *citrus* authority. In addition, 'Sonet' is free from Apple Stem grooving virus (*Capillovirus* spp.), psorosis virus (Ophiovirus), Impietratura (*Citrus impietratura* agent (CSI000)), *Citrus* Viroids (CVD I: Genus *Apscaviroid* species: *Citrus viroid* CVd-I (CBLVd), CVD II: Genus *Hostuviroid* species: *Citrus viroid* CVd-II (HSVd), CVD III: Genus *Apscaviroid* species: *Citrus viroid* III (CVd-III), CVD IV: Genus *Cocadviroid* species: *Citrus viroid* IV (CVd-IV), CVD V: Genus *Apscaviroid* species: *Citrus viroid* V (CVd-V)), and Exocortis (Family Pospiviroidae, Genus *Pospiviroid*, species *citrus exocortis viroid* CEVd).

The present variety is distinguishable over 'Miho Wase' Satsuma (*Citrus unshiu*) which is as the closest variety to 'Sonet', in the following ways. 'Sonet' differs in leaf morphology from the 'Miho Wase', matures about two weeks later than the 'Miho Wase', has a smoother firmer and tighter rind, does not puff easily, and has improved flavour over 'Miho Wase'. Fruit of 'Sonet' could contain some seed under cross pollination conditions, while fruit of 'Miho Wase' will be seedless under similar conditions. 'Sonet' matures earlier than any of its possible male pollen parents.

BRIEF SUMMARY OF THE INVENTION

This invention relates to a new and distinct variety of a Satsuma hybrid (*Citrus unshiu* X), presently named 'Sonet' the novel characteristics of which, under the local South African evaluation conditions, reside particularly in the early onset of maturity of the fruit, as well as a firmer fruit rind, does not puff easily and has improved flavour over 'Satsuma' and early 'Clementine' maturing at this time. Under local conditions, fruit maturity takes between 812 to 820 days after fruit-set. Ploidy level is unknown but presumed to be polyploid.

DETAILED BOTANICAL DESCRIPTION

Figure 1:
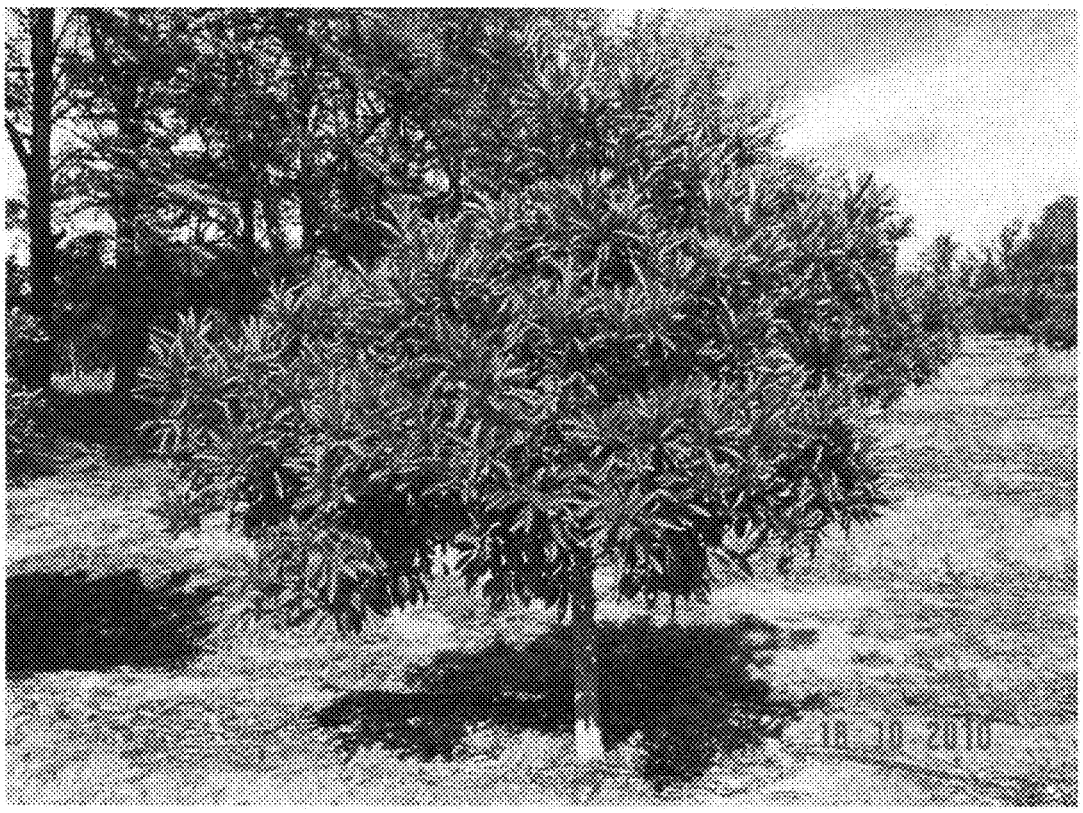
FIG. 1: is a photograph showing an entire 'Sonet' tree on 'Carrizo citrange' rootstock at four years of age.
Figure 2:
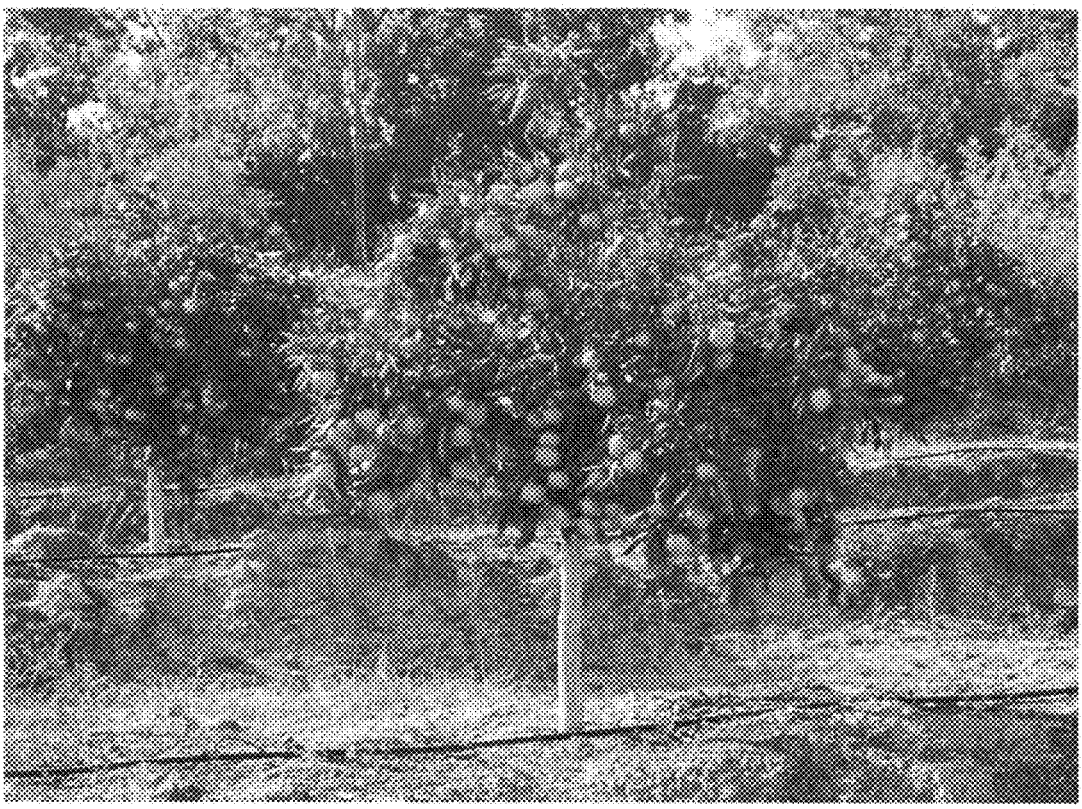
FIG. 2: is a photograph showing crop load potential of 'Sonet' at three years of age.
Figure 3:
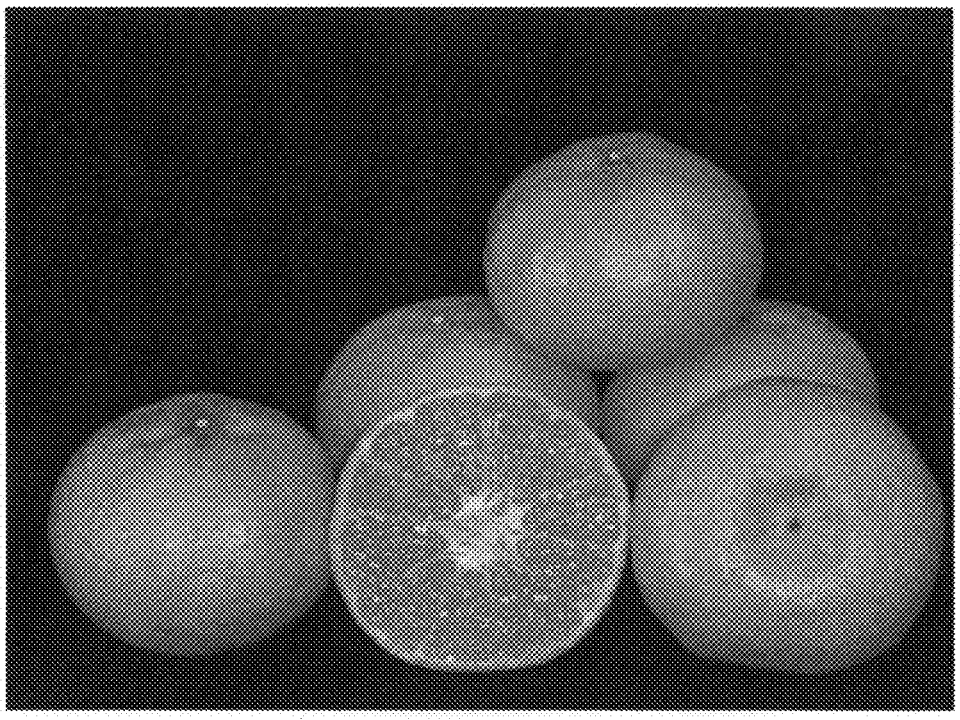
FIG. 3: is a photograph of 'Sonet' fruit in perspective view showing its general shape.
Figure 4:
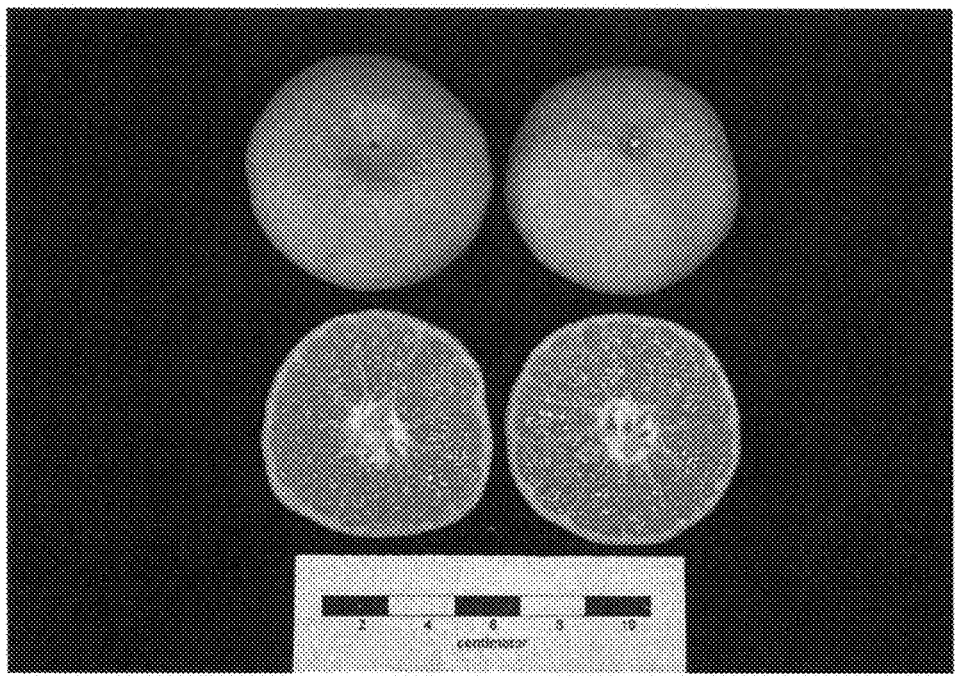
FIG. 4: is a further photograph showing details of a typical 'Sonet' fruit: viewed from top and bottom aspects showing the apex and base, respectively, together with a cross section through the fruit.
Figure 5:
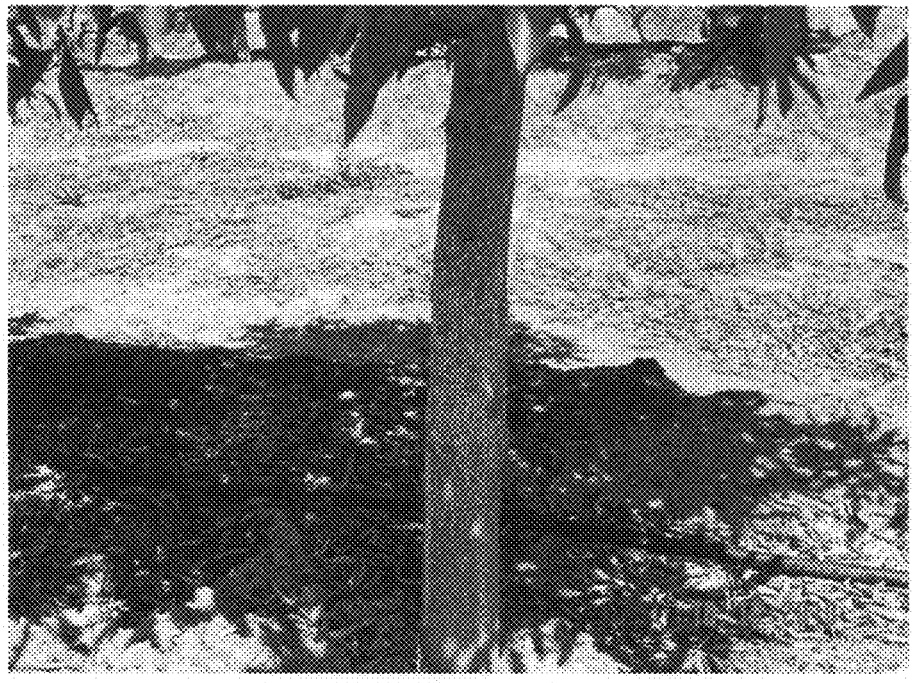
FIG. 5: is a photograph depicting a typical stem of 'Sonet', and in particular showing bud union.
Figure 6:
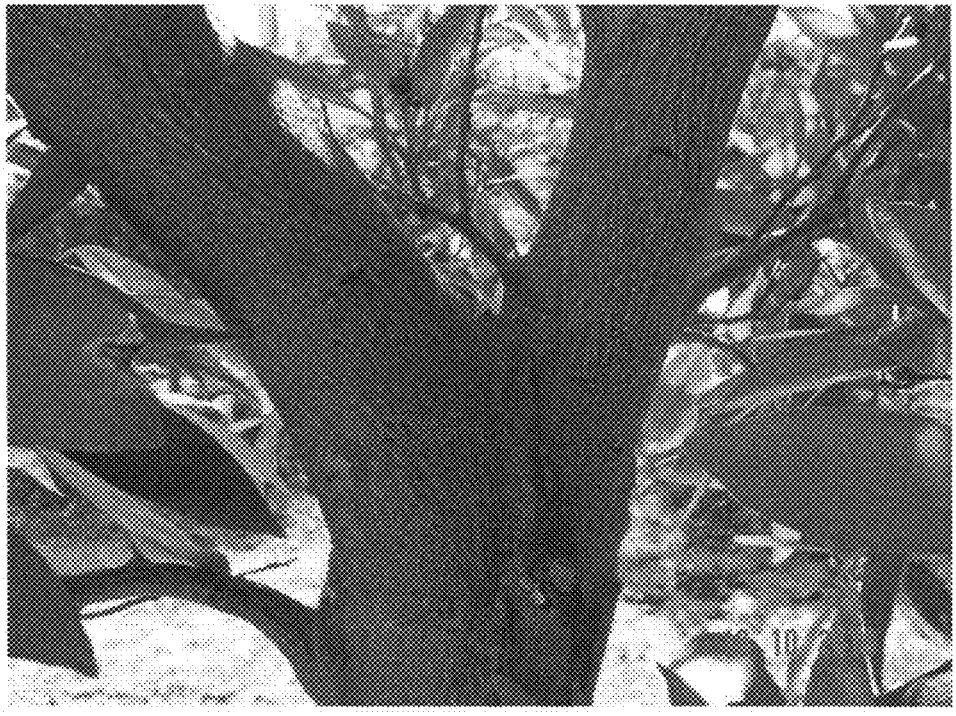
FIG. 6: is a photograph depicting a close up of the bark on 'Sonet'.
Figure 7:
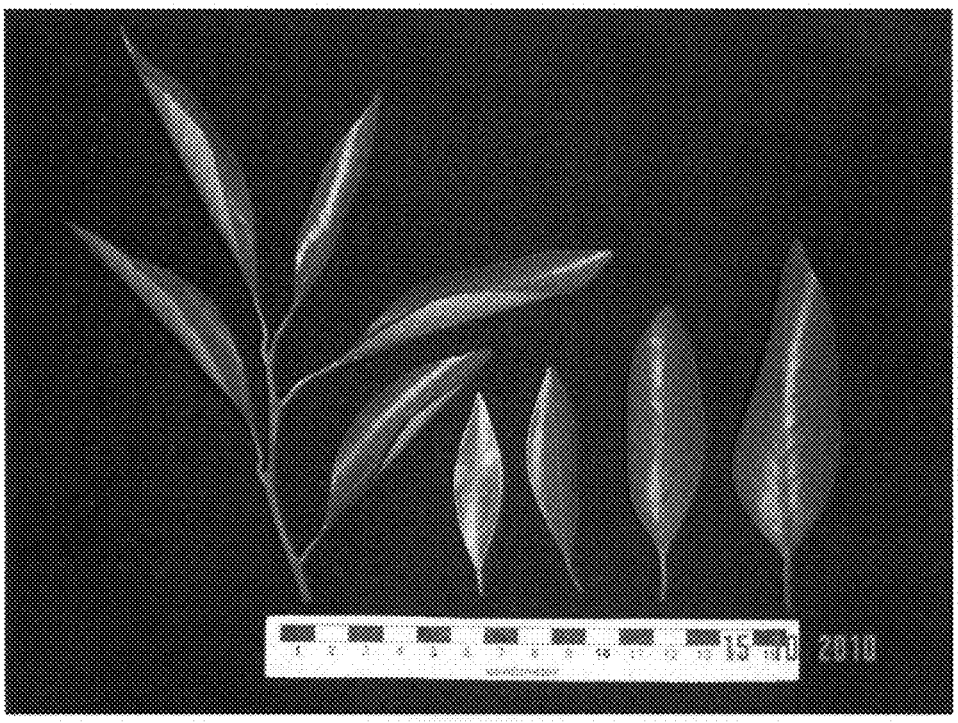
FIG. 7: is a close-up photograph showing several leaves of 'Sonet', illustrating the sizes and shapes of the leaves, including the venation thereof.
Figure 8:
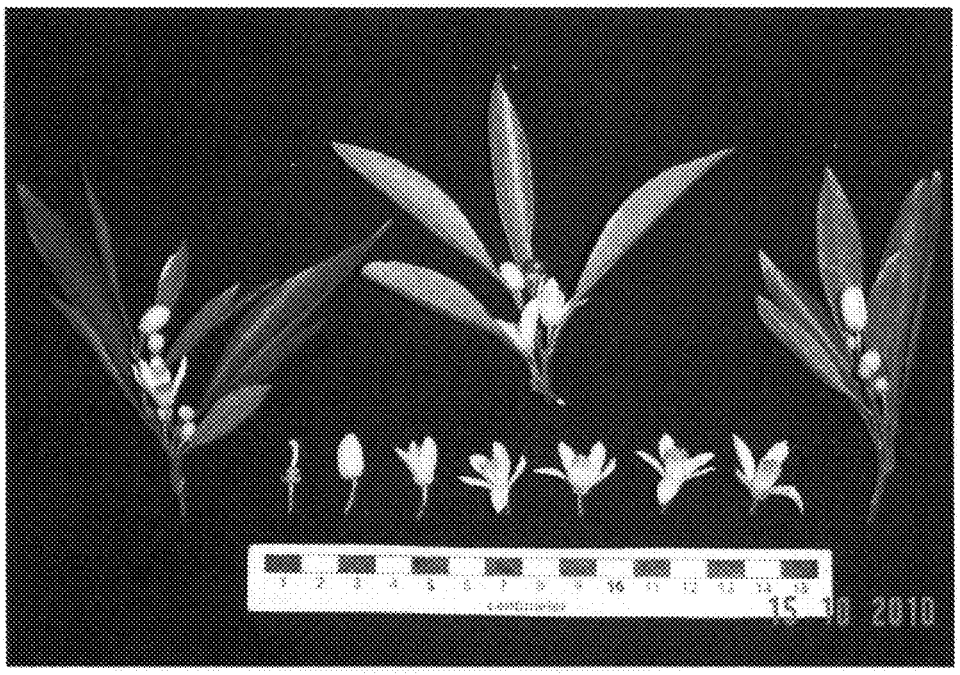
FIG. 8: is a photograph showing florescence.
Figure 9:
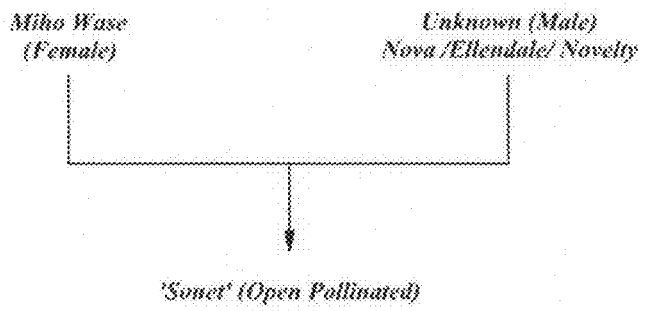
FIG. 9: is a schematic illustration of the pedigree of 'Sonet'.

The detailed description below is based on four year old trees, unless otherwise specifically stated to the contrary.

Tree: 'Sonet' trees are compact and Satsuma-like with a Clementine-like leaf shape. The tree is precocious and heavy bearing, and has a spreading growth habit. Thorns have been observed on some nursery trees and on juvenile trees. However older bearing trees have very small to no thorns. Observed juvenile thorniness is probably attributable to shoot-tip grafting (STG). Thorniness appears to be reduced and in some cases eliminated through successive growth cycles, notably after the third successive flush. The rootstock compatibility with 'Carrizo citrange' is good as observed and indicated by stem measurements.

*Size.*—The average height of trees is 1.8 meters, measured from soil level, with an average skirt height of 0.75 meters. The average spread (width) of trees is 1.5 meters.

*Shape.*—Obloid in shape.

*Trunk.*—The trunk has a fairly smooth surface texture and is brown-green (RHS 200A and RHS 137A) in color. The average trunk diameter is 24.0 centimeters measured at the bud union. Average diameters of 19.5 centimeters and 25.5 centimeters were measured at heights of 15 centimeters above and below the bud union, respectively. The average height of the bud union is 28 centimeters, measured above soil level.

*Branch.*—Branches have a diameter of between 8.2 and 13.4 centimeters. There are between 5 and 8 main branches per tree. Average crotch angles vary between 30° and 90°. The smaller of the range of crotch angles is found among the middle vertically growing branches forming the top of the tree, and the larger of the range of crotch angles is found between the vertically growing branches and the horizontally growing branches, forming the sides of the tree. As with the trunk, the branches have a fairly smooth surface texture and are brown-green (RHS 199B and RHS 137A) in color.

Flower:

*Size and color.*—The flower of 'Sonet' is typically hermaphroditic. Its petals are yellow-white (RHS 158D) on the inside and yellow-white (RHS 158D) with small yellow (RHS 4B) speckles on the outside. Further, it has light yellow (RHS 11A) anthers. Flowering occurs from September to October in South Africa. Being a normal diploid Satsuma, there is a small to medium amount of pollen with approximately 63% viability depending on climatic conditions, and as determined using the carmine-red stain method. Flower buds are ovoid in shape and have an average length of 11.5 millimeters and an average width of 6.1 millimeters. In addition, each flower has five petals. Petals are elliptic in shape and have an average length and width of 14.0 millimeters and 5.6 millimeters, respectively. The petal tip is acute in shape, while the base is truncate. The petal margin is entire. On a completely opened flower, the typical calyx diameter averages 5.0 millimeters. There are generally three to five flowers per cluster and the flowers have a typical *citrus* flower fragrance.

*Reproductive organs.*—The style has a length of 5.5 millimeters, while the stigma and the style, in combination, are approximately 7.2 millimeters long. The stamen has a length of 7.4 millimeters. The style is white-green (RHS 145B), while the stigma is light yellow (RHS 11B) in an unpollinated state. On average, there is one style and stigma, and 14 to 20 stamens with anthers. The style with the stigma is the same length as the stamens positioning the anthers around, at the same height as, the stigma.

Leaves: For purposes of the following leaf description, all leaves were taken as the first leaf after the new flush growth.

*Shape and size.*—Leaves are simple, brevipetiolate and lanceolate in shape, with very slight dentate incisions along the blade margin. Blade emargination is not present at the tip. The leaves also have typically pinnate venation. The shape of the leaf apex is acute while the base is cuneate. In cross-section, the blade shape is straight but fairly concave. The length of a typical leaf blade is approximately 80.2 millimeters in length and the leaf blade also has a width of approximately 28.5 millimeters. The ratio of length: width of the typical leaf is 2.8:1. Generally speaking, the shape and size of the 4-year old 'Sonet' trees differ from the mother tree in that the leaves are smaller and narrower in shape and are lighter in colour. Leaf twisting and blistering are both absent or weak.

*Petiole.*—Wings are present but not prominent and are linear and narrow. Width of the wings is 2 millimeters. Length of the petiole is approximately 11 millimeters.

*Color and surface texture.*—The adaxial (leaf upper) surface is darker (RHS 137A), in comparison to the abaxial (leaf lower) surface (RHS 137C). The leaf upper and lower surfaces are smooth and leaf veins are not prominent.

Fruit, external characteristics:

*Color.*—The rind color is Yellow-green (RHS 15A and 17A) to Yellow-orange (RHS 21A and 23 A) when the fruit is fully mature.

*Rind.*—Fruit is easy to peel and the rind has an average thickness of 1.5 to 2 millimeters. The strength of the fruit rind is weak to medium.

*Oil glands.*—Small oil glands are present, not protruding and are uniform in size. Oiliness is dry to medium.

*Surface.*—Pubescence is absent on the fruit surface, and the fruit surface is fairly smooth in appearance. Overall, the fruit has a medium glossy appearance (UPOV 5 — see ON 285 TG/201/1).

*Shape.*—With reference to the *Citrus* descriptors of the previously named International Plant Genetic Resources Institute (IPGRI), now known as Biodiversity International, the shape of 'Sonet' is obloid, having its broadest part in the middle of the fruit. The general shape of the proximal part (stem end) of the fruit is slightly rounded with a slight ruffling around the stem, while the fruit apex (flower end) is depressed.

*Size.*—Fruit is on average 42 millimeters in length and 65 to 85 millimeters in diameter. Individual fruit mass varies between 68 grams to 96 grams with an average mass of 83 grams per fruit (see Table 1 below) on 'Carrizo citrange' rootstock. The fruit length:diameter ratio is 0.742.

*Base.*—Depressed.

*Calyx.*—Slightly rounded.

*Apex.*—Slightly rounded.

*Areola.*—Present and smooth, with a diameter of 21.1 millimeters.

*Stylar scar.*—Present, but small in size.

Fruit, internal characteristics:

*Color.*—The internal flesh color is orange (RHS 23A) to dark orange (RHS 24A) when the fruit is fully mature.

*Navel.*—Absent when fruit is viewed internally.

*Glandular layer.*—Thickness of the rag is normal and slightly tough.

*Mesocarp* (*albedo*).—The adherence of the albedo to the pulp is weak and thus the peel is reasonably easy to remove from the pulp. No albedo strands are left behind after such removal. The albedo color is yellow-orange (RHS 158D). The albedo has medium density. The albedo has medium density.

*Axis.*—Fruit has an open core with a diameter of approximately 15 millimeters. Further, the core has sparse to no filling.

*Segments.*—Each fruit has ten to twelve segments, and on average there are eleven well-developed segments per fruit. Strength of the segment is medium.

*Pulp.*—The pulp is fine with large cells. In a transverse section of the fruit, the shape of the fruit pulp is scalloped.

*Neck/collar.*—A collar on the fruit is sometimes present, but mostly absent. Height of the collar when present is low to medium. Diameter of the collar when present is 26.4 millimeters. Neck on the fruit is absent.

*Juice.*—Fruit is juicy with a good flavor that is aligned towards a mandarin-like flavour. Juice is yellow-orange (RHS 21B) in color. Fruit have an average juice percentage of 59.5% on 'Carrizo citrange' rootstock. As indicated by the solids:acid ratio (see Table 1), the best time to harvest fruit under South African conditions is early to mid April.

*Seeds.*—Seeds are mostly clavate in shape (about 75%), however some are semi-deltoid in shape (about 25%), with a mostly wrinkled surface. In this regard, approximately 30% of the seed surface tends to be smooth. The clavate shaped seeds have an average length of 10.3 millimeters and an average width of 4.8 millimeters, while the semi-deltoid shaped seeds have an average length of 8.0 millimeters and an average width of 6.0 millimeters. Further, the seeds have a grey-white (RHS 196B) external color, and are green (RHS 160B) and highly poly-embryonic after removal of the testa. This variety is parthenocarpic. However it contains few (1 to 3) to no seeds in solid blocks (as seen in Table 1). In mixed blocks where cross pollination is present, fruit do contain more seed.

TABLE 1

'Sonet' Satsuma hybrid: Internal Quality Tests - 2010 (trees 4 years old, planted in 1996) Addo, Eastern Cape, South Africa:

| Cultivar | Root-stock | Test date | Juice % | Brix % | Acid % | Brix:Acid Ratio | Percentage fruit with 0 seed per fruit | 1-3 | 4-6 | 7+ | Avg. Fruit Mass (grams) |
|---|---|---|---|---|---|---|---|---|---|---|---|
| 'Sonet' | Carrizo | 24 Mar. 2010 | 60.0 | 12.0 | 1.34 | 9.0 | 62 | 18 | 5 | 3 | 79.1 |
| 'Sonet' | Carrizo | 20 Apr. 2010 | 59.0 | 12.6 | 1.00 | 12.6 | 54 | 8 | 0 | 1 | 85.5 |

TABLE 2

Internal Quality Tests (trees topworked in 2000 to 'Carrizo citrange' rootstocks) Addo, Eastern Cape, South Africa:

| Test Date | Juice % | Brix % | T. Acid % | Brix/TA Ratio |
|---|---|---|---|---|
| 14 Apr. 2008 | 67.4 | 11.8 | 1.08 | 10.9 |
| 09 Apr. 2010 | 58.2 | 9.8 | 1.05 | 9.3 |

*Yield.*—The average fruit yields across the time period 2009-2010 appear in Table 3 below:

TABLE 3

Average Fruit Yield (2009-2010) Addo, Eastern Cape, South Africa:

| | Year 2009 | 2010 |
|---|---|---|
| Tree age (years) | 3 | 4 |
| Yield (kg fruit/tree) | 20.1 | 32.9 |
| Yield (ton/ha) | 11.1 | 18.3 |

The fruit of 'Sonet' is intended for human consumption. Fruit stored and shipped at 4° C., and kept under these conditions, are likely to keep for up to six weeks. Data of a cold sterilization trial indicate that 91% of the fruit is marketable after storage for 32 days at −0.5 Celsius and 7 days at ambient temperature. Optimal protocols for degreening and waxing is required for extension of shelf life. The time of maturity of the fruit is end-March to mid-April, which makes this selection an early maturing variety. The variety is self-compatible.

The above-described new variety of Satsuma hybrid displays a distinct early expression of maturity (early to mid April), as well as an improved flavour and firmer fruit and tighter rind and does not puff easily, compared to known varieties of Satsuma ripening at this time.

What we claim is:

1. A novel and distinct Satsuma hybrid tree having the characteristics described and illustrated herein.

* * * * *